United States Patent

Bennett

Patent Number: 6,063,881
Date of Patent: May 16, 2000

[54] OLIGOMERIZATION OF PROPYLENE

[75] Inventor: Alison Margaret Anne Bennett, Wilmington, Del.

[73] Assignee: E. I. du Pont de Nemours and Company, Wilmington, Del.

[21] Appl. No.: 09/053,944

[22] Filed: Apr. 2, 1998

[51] Int. Cl.[7] ........................................ C08F 4/44
[52] U.S. Cl. .................. 526/161; 526/169.1; 526/171; 526/172; 526/351; 585/527; 585/531
[58] Field of Search ................. 526/161, 169.1, 526/171, 172; 585/527, 531; 1/531

[56] References Cited

U.S. PATENT DOCUMENTS 5,955,555  9/1999  Bennett ............................. 526/133

FOREIGN PATENT DOCUMENTS

| WO 96/23010 | 8/1996 | WIPO | C08F 210/16 |
| WO 98/27124 | 6/1998 | WIPO | C08F 10/00 |
| WO 98/30612 | 7/1998 | WIPO | C08F 10/06 |
| WO 99/02472 | 1/1999 | WIPO | C07C 2/32 |
| WO 99/12981 | 3/1999 | WIPO | C08F 4/70 |

OTHER PUBLICATIONS

Sacconi et al., High–spin Five–coordinate Nickel(II) and Cobalt(II) Complexes with 2,6–Diacetylpyridinebis(imines), J. Chem. Soc. A, pp. 1510–1515, 1968.

Curry et al., Metal Complexes Derived from Substituted Hydrazones of 2,6–Diacetylpyridine, Inorg. Chem. vol. 6. No. 8, pp. 1570–1571, 1967.

Britovsek et al., Novel olefin polymerization catalysts based on iron and cobalt, Chem. Commun., pp. 849–850, 1998.

*Primary Examiner*—David W. Wu
*Assistant Examiner*—Roberto Rabago
*Attorney, Agent, or Firm*—Joel D. Citron; Craig H. Evans; Bart E. Lerman

[57] ABSTRACT

Propylene may be oligomerized by contact with cobalt complexes corresponding to the following structure:

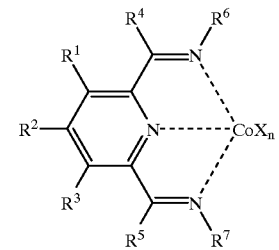

wherein $R^1$–$R^7$ are hydrogen, hydrocarbyl or inert functional groups, and X is an anion. The resulting olefins are useful as chemical intermediates.

18 Claims, No Drawings

OLIGOMERIZATION OF PROPYLENE

FIELD OF THE INVENTION

Selected cobalt complexes of 2,6-pyridinecarboxaldehydebis(imines) and 2,6-diacylpyridinebis(imines) are catalysts for the oligomerization of propylene.

BACKGROUND OF THE INVENTION

Oligomers of propylene such as propylene trimer and tetramer are made commercially by several different processes. These compounds are useful as chemical intermediates. For instance phenol may be alkylated with propylene trimer and/or tetramer, and subsequently ethoxylated to form a commercial industrial detergent.

Certain iron and/or cobalt complexes of selected 2,6-pyridinecarboxaldehydebis(imines) and 2,6-diacylpyridinebis(imines) have been reported in co-pending applications to polymerize and/or oligomerize ethylene, see U.S. patent applications Ser. No. 08/991372, filed Dec. 16, 1997, now U.S. Pat. No. 5,955,555 and Ser. No. 09/005965, filed Jan. 12, 1998.

Certain iron complexes of selected 2,6-pyridinecarboxaldehydebis(imines) and 2,6-diacylpyridinebis(imines) have been reported in co-pending application to polymerize and/or oligomerize propylene, see U.S. patent application Ser. No. 09/006031, filed Jan. 12, 1998.

SUMMARY OF THE INVENTION

This invention concerns a first process for the oligomerization of propylene, comprising, contacting, at a temperature of about −100° C. to about +200° C., a compound of the formula

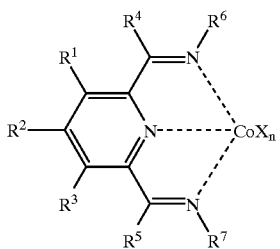

(II)

with propylene and:
(a) a first compound W, which is a neutral Lewis acid capable of abstracting $X^-$ and alkyl group or a hydride group from M to form $WX^-$, $(WR^{20})^-$ or $WH^-$ and which is also capable of transferring an alkyl group or a hydride to cobalt, provided that $WX^-$ is a weakly coordinating anion; or
(b) a combination of second compound which is capable of transferring an alkyl or hydride group to cobalt and a third compound which is a neutral Lewis acid which is capable of abstracting $X^-$, a hydride or an alkyl group from M to form a weakly coordinating anion;

wherein:
each X is an anion;
n is 1, 2 or 3 so that the total number of negative charges on said anion or anions is equal to the oxidation state of a Co atom present in (II);
$R^1$, $R^2$ and $R^3$ are each independently hydrogen, hydrocarbyl, substituted hydrocarbyl, or an inert functional group;

$R^4$ and $R^5$ are each independently hydrogen, hydrocarbyl, an inert functional group or substituted hydrocarbyl;
$R^6$ and $R^7$ are aryl or substituted aryl; and
$R^{20}$ is alkyl.

This invention also concerns a second process for the oligomerization of propylene, comprising contacting, at a temperature of about −100° C. to about +200° C., a Co[II] or Co[III] complex of a tridentate ligand of the formula

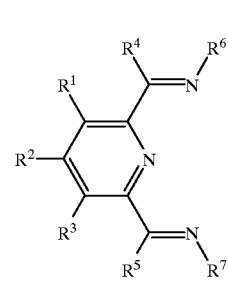

(I)

with propylene, wherein:
$R^1$, $R^2$ and $R^3$ are each independently hydrogen, hydrocarbyl, substituted hydrocarbyl, or an inert functional group;
$R^4$ and $R^5$ are each independently hydrogen, hydrocarbyl, an inert functional group or substituted hydrocarbyl; and
$R^6$ and $R^7$ are aryl or substituted aryl;
and provided that a Co[II] or Co[III] atom also has bonded to it an empty coordination site or a ligand that may be displaced by said propylene, and a ligand that may add to said propylene.

DETAILS OF THE INVENTION

Herein, certain terms are used. Some of them are:

A "hydrocarbyl group" is a univalent group containing only carbon and hydrogen. If not otherwise stated, it is preferred that hydrocarbyl groups herein contain 1 to about 30 carbon atoms.

By "substituted hydrocarbyl" herein is meant a hydrocarbyl group which contains one or more substituent groups which are inert under the process conditions to which the compound containing these groups is subjected. The substituent groups also do not substantially interfere with the process. If not otherwise stated, it is preferred that substituted hydrocarbyl groups herein contain 1 to about 30 carbon atoms. Included in the meaning of "substituted" are heteroaromatic rings.

By "(inert) functional group" herein is meant a group other than hydrocarbyl or substituted hydrocarbyl which is inert under the process conditions to which the compound containing the group is subjected. The functional groups also do not substantially interfere with any process described herein that the compound in which they are present may take part in. Examples of functional groups include halo (fluoro, chloro, bromo and iodo), ether such as —$OR^{18}$ wherein $R^{18}$ is hydrocarbyl or substituted hydrocarbyl. In cases in which the functional group may be near a cobalt atom, such as $R^4$, $R^5$, $R^8$, $R^{12}$, $R^{13}$, and $R^{17}$ the functional group should not coordinate to the metal atom more strongly than the groups in compounds containing $R^4$, $R^5$, $R^8$, $R^{12}$, $R^{13}$, and $R^{17}$ which are shown as coordinating to the metal atom, that is they should not displace the desired coordinating group.

By an "alkyl aluminum compound" is meant a compound in which at least one alkyl group is bound to an aluminum atom. Other groups such as alkoxide, hydride, and halogen may also be bound to aluminum atoms in the compound.

By "neutral Lewis base" is meant a compound, which is not an ion, which can act as a Lewis base. Examples of such compounds include ethers, amines, sulfides, and organic nitriles.

By "cationic Lewis acid" is meant a cation which can act as a Lewis acid. Examples of such cations are sodium and silver cations.

By relatively noncoordinating (or weakly coordinating) anions are meant those anions as are generally referred to in the art in this manner, and the coordinating ability of such anions is known and has been discussed in the literature, see for instance W. Beck., et al., Chem. Rev., vol. 88 p. 1405–1421 (1988), and S. H. Stares, Chem. Rev., vol. 93, p. 927–942 (1993), both of which are hereby included by reference. Among such anions are those formed from the aluminum compounds in the immediately preceding paragraph and $X^-$, including $R^9{}_3AlX^-$, $R^9{}_2AlClX^-$, $R^9AlCl_2X^-$, and "$R^9AlOX^-$", wherein $R^9$ is alkyl. Other useful noncoordinating anions include $BAF^-$ {BAF=tetrakis[3,5-bis(trifluoromethyl)phenyl]borate}, $SbF_6{}^-$, $PF_6{}^-$, and $BF_4{}^-$, trifluoromethanesulfonate, p-toluenesulfonate, $(R_fSO_2)_2N^-$, and $(C_6F_5)_4B^-$.

By an empty coordination site is meant a potential coordination site that does not have a ligand bound to it. Thus if an ethylene molecule is in the proximity of the empty coordination site, the ethylene molecule may coordinate to the metal atom.

By a ligand that may add to propylene is meant a ligand coordinated to a metal atom into which an ethylene molecule (or a coordinated ethylene molecule) may insert to start or continue a polymerization. For instance, this may take the form of the reaction (wherein L is a ligand):

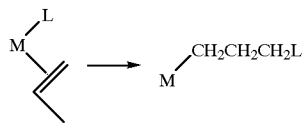

Note the similarity of the structure on the left-hand side of this equation to compound (IX) (see below).

By oligomerization is meant that at least 50 mole percent of the oligomerized product has 18 or fewer carbon atoms.

Compounds useful as ligands herein in cobalt complexes are diimines of 2,6-pyridinedicarboxaldehyde or 2,6-diacylpyridines of the general formula

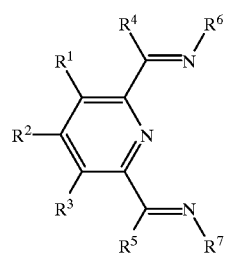

wherein $R^1$, $R^2$ and $R^3$ are each independently hydrogen, hydrocarbyl, substituted hydrocarbyl, or an inert functional group, $R^4$ and $R^5$ are each independently hydrogen, hydrocarbyl, an inert functional group or substituted hydrocarbyl, and $R^6$ and $R^7$ are aryl or substituted aryl.

(IV) may be made by the reaction of a compound of the formula

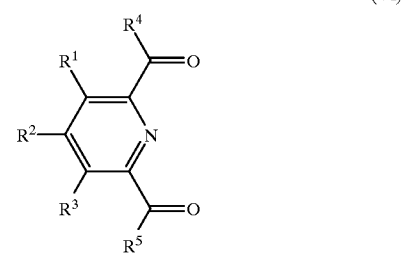

with a compound of the formula $H_2NR^6$ or $H_2NR^7$, wherein $R^1$, $R^2$ and $R^3$ are each independently hydrogen, hydrocarbyl, substituted hydrocarbyl, or an inert functional group, $R^4$ and $R^5$ are each independently hydrogen, hydrocarbyl or substituted hydrocarbyl. Preferably $R^4$ and $R^5$ are each hydrogen or hydrocarbyl, and $R^6$ and $R^7$ are aryl or substituted aryl. These reactions are often catalyzed by carboxylic acids, such as formic acid.

Preferred compounds of formula (IV) and compounds in which (IV) is a ligand, whether present in compounds such as (I), (II), (VII), (IX) and (XII) a preferred compound is (III), which is a subset of (IV).

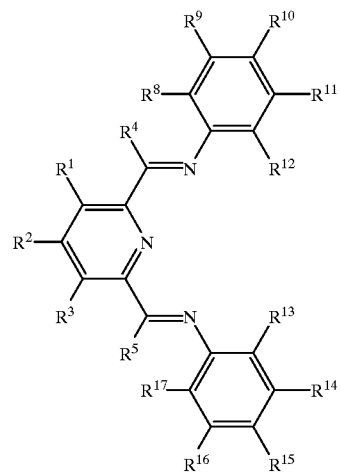

In (III), and hence in (I), (II), (IV), (VII), (IX) and (XII) that match the formula of (III), it is preferred that:

$R^1$, $R^2$ and $R^3$ are hydrogen; and/or $R^9$, $R^{10}$, $R^{11}$, $R^{14}$, $R^{15}$ and $R^{16}$ is each independently halogen, alkyl containing 1 to 6 carbon atoms, or hydrogen, and it is more preferred that each of these is hydrogen; and/or $R^{10}$ and $R^{15}$ are methyl; and/or $R^8$ and $R^{13}$ is each independently halogen, phenyl or alkyl containing 1 to 6 carbon atoms, and it is especially preferred that each $R^8$ and $R^{13}$ is alkyl containing 1–6 carbon atoms, and it is more preferred that $R^8$ and $R^{13}$ are i-propyl or t-butyl;

$R^{12}$ and $R^{17}$ is each independently halogen, phenyl, hydrogen, or alkyl containing 1 to 6 carbon atoms, and it is especially preferred that each $R^{12}$ and $R^{17}$ is alkyl containing 1–6 carbon atoms, and it is more preferred that $R^{12}$ and $R^{17}$ are i-propyl, or it is especially preferred that $R^{12}$ and $R^{17}$ are hydrogen;

$R^4$ and $R^5$ are each independently hydrogen or alkyl containing 1 to 6 carbon atoms, and it is especially preferred that $R^4$ and $R^5$ are each independently hydrogen or methyl.

Also in (IV), and hence in (I), (II), (VII), (IX) and (XII), it is preferred that:

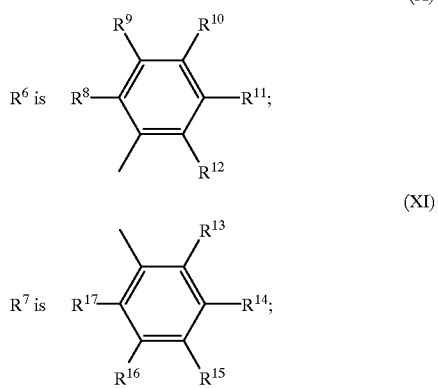

$R^8$ and $R^{13}$ are each independently hydrocarbyl, substituted hydrocarbyl or an inert functional group;

$R^9$, $R^{10}$, $R^{11}$, $R^{14}$, $R^{15}$ and $R^{16}$ are each independently hydrogen, hydrocarbyl, substituted hydrocarbyl or an inert functional group;

$R^{12}$ and $R^{13}$ are each independently hydrogen, hydrocarbyl, substituted hydrocarbyl or an inert functional group;

and provided that any two of $R^8$, $R^9$, $R^{10}$, $R^{11}$, $R^{12}$, $R^{13}$, $R^{14}$, $R^{15}$, $R^{16}$ and $R^{17}$ that are vicinal to one another, taken together may form a ring.

It is believed that the bulkiness of $R^6$ and/or $R^7$ become help to determine what oligomers are produced, that is how many propylene molecules are in the resulting oligomer, on average. Another was of stating this is that this bulkiness controls the average molecular weight of the product. It is believed that as $R^6$ and/or $R^7$ become bulkier, the average molecular weight of the oligomer produced will increase. However, other effects (some unwanted), such as effects on yields may also occur.

Specific preferred compounds (III) [and also in (I), (II), (IV), (VII), (IX) and (XII)] are:

$R^1$, $R^2$, $R^3$, $R^9$, $R^{10}$, $R^{11}$, $R^{14}$, $R^{15}$ and $R^{16}$ are hydrogen, $R^8$ and $R^{13}$ are chloro, and $R^4$, $R^5$, $R^{12}$ and $R^{17}$ are methyl;

$R^1$, $R^2$, $R^3$, $R^9$, $R^{10}$, $R^{11}$, $R^{12}$, $R^{14}$, $R^{15}$, $R^{16}$ and $R^{17}$ are hydrogen, $R^4$ and $R^5$ are methyl, and $R^8$ and $R^{13}$ are phenyl;

$R^1$, $R^2$, $R^3$, $R^4$, $R^5$, $R^9$, $R^{10}$, $R^{11}$, $R^{12}$, $R^{14}$, $R^{15}$, $R^{16}$ and $R^{17}$ are hydrogen, and $R^8$ and $R^{13}$ are phenyl;

$R^1$, $R^2$, $R^3$, $R^4$, $R^5$, $R^9$, $R^{10}$, $R^{11}$, $R^{14}$, $R^{15}$, and $R^{16}$ are hydrogen, and $R^8$, $R^{12}$, $R^{13}$ and $R^{17}$ are i-propyl; and $R^1$, $R^2$, $R^3$, $R^9$, $R^{10}$, $R^{11}$, $R^{12}$, $R^{14}$, $R^{15}$, $R^{16}$ and $R^{17}$ are hydrogen, $R^4$ and $R^5$ are methyl, and $R^8$ and $R^{13}$ are t-butyl.

In the oligomerization processes described herein, it can be seen from the results that it is preferred that there be at least some steric crowding caused by the tridentate ligand about the Co atom. Therefore, it is preferred that groups close to the metal atom be relatively large. It is relatively simple to control steric crowding if (III) is the tridentate ligand, since control of steric crowding can be achieved simply by controlling the size of $R^8$, $R^{12}$, $R^{13}$ and $R^{16}$. These groups may also be part of fused ring systems, such as 9-anthracenyl.

In the first polymerization process it is preferred that X is chloride, bromide and tetrafluoroborate.

In the first polymerization process described herein a cobalt complex (II) is contacted with ethylene and a neutral Lewis acid W capable of abstracting $X^-$, hydride or alkyl from (II) to form a weakly coordinating anion, and must alkylate or be capable of adding a hydride ion to the metal atom, or an additional alkylating agent or an agent capable of adding a hydride anion to the metal atom must be present. The neutral Lewis acid is originally uncharged (i.e., not ionic). Suitable neutral Lewis acids include $SbF_5$, $Ar_3B$ (wherein Ar is aryl), and $BF_3$. Suitable cationic Lewis acids or Bronsted acids include NaBAF, silver trifluoromethanesulfonate, $HBF_4$, or $[C_6H_5N(CH_3)_2]^+$ $[B(C_6F_5)_4]^-$. In those instances in which (II) (and similar catalysts which require the presence of a neutral Lewis acid or a cationic Lewis or Bronsted acid), does not contain an alkyl or hydride group already bonded to the metal atom, the neutral Lewis acid or a cationic Lewis or Bronsted acid also alkylates or adds a hydride to the metal or a separate alkylating or hydriding agent is present, i.e., causes an alkyl group or hydride to become bonded to the metal atom.

It is preferred that $R^{20}$ contains 1 to 4 carbon atoms, and more preferred that $R^{20}$ is methyl or ethyl.

For instance, alkyl aluminum compounds (see next paragraph) may alkylate (II). However, not all alkyl aluminum compounds may be strong enough Lewis acids to abstract $X^-$ or an alkyl group from the metal atom. In that case a separate Lewis acid strong enough to do the abstraction must be present. For instance, in Example 39, polymethylaluminoxane is used as the "sole" Lewis acid, it both alkylates and does the abstraction from the metal atom.

A preferred neutral Lewis acid, which can alkylate the metal, is a selected alkyl aluminum compound, such as $R^{20}{}_3Al$, $R^{20}AlCl_2$, $R^{20}{}_2AlCl$, and "$R^{20}AlO$" (alkylaluminoxanes), wherein $R^{20}$ is alkyl containing 1 to 25 carbon atoms, preferably 1 to 4 carbon atoms. Suitable alkyl aluminum compounds include methylaluminoxane (which is an oligomer with the general formula $[MeAlO]_n$), modified $[MeAlO]_n$ wherein a minority of the methyl groups are replaced by another alkyl group, $(C_2H_5)_2AlCl$, $C_2H_5AlCl_2$, and $[(CH_3)_2CHCH_2]_3Al$.

Metal hydrides such as $NaBH_4$ may be used to bond hydride groups to the metal M.

In the second polymerization process described herein a cobalt complex of (I) is either added to the polymerization process or formed in situ in the process. In fact, more than one such complex may be formed during the course of the process, for instance formation of an initial complex and then reaction of that complex to form a living ended polymer containing such a complex.

Examples of such complexes which may be formed initially in situ include

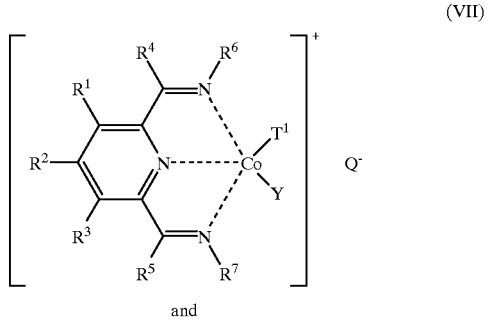

and

-continued

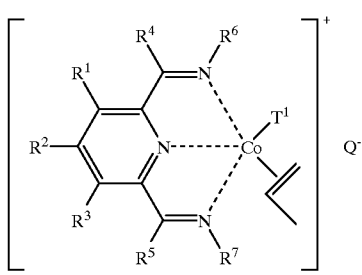

(XII)

wherein $R^1$ through $R^7$ are as defined above, $T^1$ is hydride or alkyl or any other anionic ligand into which propylene can insert, Y is a neutral ligand capable of being displaced by propylene or a vacant coordination site, and Q is a relatively non-coordinating anion. Complexes may be added directly to the process or formed in situ. For instance, (VII) may be formed by the reaction of (II) with a neutral Lewis acid such as an alkyl aluminum compound. Another method of forming such a complex in situ is adding a suitable cobalt compound such as cobalt [II] acetylacetonate, (I) and an alkyl aluminum compound. Other metal salts in which anions similar to acetylacetonate are present, and which may be removed by reaction with the Lewis or Bronsted acid. For instance metal halides and carboxylates (such as acetates) may be used, particularly if they are slightly soluble in the process medium. It is preferred that these precursor metal salts be at least somewhat soluble in the process medium.

After the propylene oligomerization has started, the complex may be in a form such as

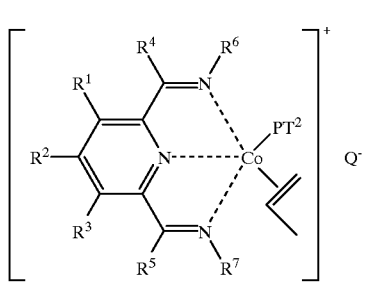

(IX)

wherein $R^1$ through $R^7$, and Q are as defined above, and P is a divalent (oligo)propylene group, and $T^2$ is an end group, for example the groups listed for $T^1$ above. Those skilled in the art will note that (IX) is in essence an oligomer containing a so-called living end. It is preferred that Co be in +2 oxidation state in (VII), (VIII) and (IX). Compounds such as (VII), (IX) and (XII) may or may not be stable away from an environment similar to that of the polymerization process, but they may be detected by NMR spectroscopy, particularly one or both of $^1$H and $^{13}$C NMR, and particularly at lower temperatures. Such techniques, especially for polymerization "intermediates" of these types are known, see for instance World Patent Application 96/23010, especially Examples 197–203, which is hereby included by reference.

In all the oligomerization processes herein, the temperature at which the propylene oligomerization is carried out is about −100° C. to about +200° C., preferably about −60° C. to about 150° C., more preferably about −50°C. to about 100° C. The propylene pressure at which the polymerization is carried out is not critical, atmospheric pressure to about 275 MPa being a suitable range.

The oligomerization processes herein may be run in the presence of various liquids, particularly aprotic organic liquids. The catalyst system, propylene, and propylene oligomer may be soluble or insoluble in these liquids, but obviously these liquids should not prevent the oligomerization from occurring. Suitable liquids include alkanes, cycloalkanes, selected halogenated hydrocarbons, (liquid) propylene and aromatic hydrocarbons. Specific useful solvents include hexane, toluene and benzene. A preferred liquid is the propylene oligomer itself.

The propylene oligomerizations herein may also initially be carried out in the solid state [assuming (II), (IV) or (VII) is a solid] by, for instance, supporting (II), (IV) or (VII) on a substrate such as silica or alumina, activating it with the Lewis (such as W, for instance an alkylaluminum compound) or Bronsted acid and exposing it to a polymerizable or oligomerizable olefin. An alternative method is to react or treat the support with W, then react the treated support with (II), (IV) or (VII). Or W and II), (IV) or (VII) can be mixed and then the support treated with the resulting solution. The support may also be able to take the place of the Lewis or Bronsted acid, for instance an acidic clay such as montmorillonite. Another method of making a supported catalyst is to start a polymerization or at least make a cobalt complex of another olefin or oligomer of an olefin such as cyclopentene on a support such as silica or alumina. These "Theterogeneous" catalysts may be used to catalyze oligomerization in the gas phase or the liquid phase. By gas phase is meant that the propylene is transported to contact with the catalyst particle while the propylene is in the gas phase.

In the Examples and Experiments, the pressures given are gauge pressures. The following abbreviations and terms are used:

Branching—reported as the number of methyl groups per 1000 methylene groups in the oligomer. Not corrected for end groups.
FW—formula weight
GC—gas chromatography
GC/MS—gas chromatography followed by mass spectrometry
GPC—gel permeation chromatography
MeOH—methanol
PMAO—polymethylaluminoxane
RT—room temperature
THF—tetrahydrofuran Experiment 1

2,6-Diacetylpyridinebis(2-chloro-6-methylphenylimine)

In a 200 mL round bottom flask, 2.0 g of 2,6-diacetylpyridine (FW 163.18, 0.0122 mole) and 50 mL of methanol were placed. Next, 3.45 g of 2-chloro-6-methylaniline (FW 141.60, 0.0245 mole) was added followed by three drops of formic acid and the solution was stirred at RT under nitrogen for four d, at which time no precipitate had formed. The reaction was then refluxed for 24 h. GC analysis indicated that reaction was incomplete. Refluxing was continued for a total of 1 week. Solvent was stripped from the reaction mixture via rotovap. Flash chromatography through a basic alumina column (eluted with hexane/ethyl acetate 20:1) lead to isolation of an oil. The oil was then crystallized from methanol/methylene chloride. Collected 0.21 g (4.2% yield) of pale yellow crystals. $^1$H-NMR (ppm, CDCl$_3$): 2.12(s, 6H), 2.32(s, 6H), 6.95(t, 2H), 7.13(d, 2H), 7.30(d, 2H), 7.92(t, 1H), 8.5(d, 2H)

Experiment 2

2,6-Diacetylpyridinebis(2-biphenylimine)

In a 100 mL round bottom flask, 0.48 g of 2,6-diacetylpyridine (FW 163.18, 0.00295 moles), 1.0 g of 2-aminobiphenyl (FW 169.23, 0.0059 moles), and 20 mL of methanol were placed. Three drops of formic acid were added and the resulting solution stirred under nitrogen. A precipitate formed after one day. This was filtered off, washed with cold methanol and dried. Collected 0.84 g (61% yield) of pale yellow solid. $^1$H NMR (ppm, CDCl$_3$): 2.15(s, 6H), 6.8(d, 2H), 7.15–7.50(m, 16H), 7.75(t, 1H), 8.10(d, 2H).

Experiment 3

2,6-Pyridinedicarboxaldehydebis (2,6-diisopropylphenylimine)

In a 35 mL round bottom flask, 0.28 g of 2,6-pyridinedicarboxaldehyde (FW 135.12, 0.00207 moles), 0.73 g of 2,6-diisopropylaniline (FW 177.29, 0.00414 moles), and 15 mL of methanol were placed. Three drops of formic acid were added and the solution stirred. A precipitate formed within 5 min. Stirring was continued overnight. The solid was filtered off, washed with cold methanol and dried. Collected 0.86 g (91.5% yield) of a pale yellow solid. $^1$H NMR (ppm, CDCl$_3$), 1.2(d, 24H), 3.0(m, 4H), 7.0–7.2(m, 6H), 8.0(t, 1H), 8.35(s, 2H), 8.4(d, 2H).

Experiment 4

2,6-Diacetylpyridinebis(2-tert-butylphenylimine)

In a 200 mL round bottom flask, 2.0 g of 2,6-diacetylpyridine (FW 163.18, 0.0122 moles) was dissolved in 25 mL of methanol. Next 3.66 g of 2-tert-butylaniline (FW 149.24, 0.0245 moles) and 3 drops of formic acid were added. A precipitate started to form after 30 min. The solution was stirred at room temperature overnight. The precipitate was filtered off, washed with cold methanol and then dried. Collected 3.88 g (75% yield) of a yellow solid. The NMR revealed the solid to be mostly the monoimine product. The above solid (3.85 g, FW 294.4, 0.013 mole) was placed into a 200 mL flask. 1.95 g of 2-t-butylaniline, methanol, and 4 drops of formic acid were added. The mixture was brought to reflux before slowly adding chloroform until all solids had dissolved. After 48 h the volume was reduced and the reaction cooled to precipitate more solids. These were isolated and recrystallized from methanol and a minimum amount of chloroform, yielding 2.8 g of product. $^1$H-NMR (ppm, CDCl$_3$) 1.4(s,18H), 2.4(s, 6H), 6.55(d, 2H), 7.1(t, 2H), 7.2(t, 2H), 7.45(d, 2H), 7.9 (t, 1H), 8.4 (d, 2H).

Experiment 5

[2,6-Diacetylpyridinebis(2-chloro-6-methylphenylimine)]cobalt[II]dichloride

In a dry, oxygen-free atmosphere CoCl$_2$ (anhydrous, 0.062 g) was dissolved in a minimum of dry THF. 2,6-Diacetylpyridinebis(2-chloro-6-methylphenylimine) (0.205 g) was added and the solution turned green and a green precipitate formed. The mixture was stirred at RT for 2 days after which the volume of the solution was reduced by half and pentane added to precipitate the product, which was filtered off, washed with pentane and dried. Yield 0.240 g.

Experiment 6

[2,6-Diacetylpyridinebis(2-biphenylimine)]cobalt[II] dichloride

In a dry, oxygen-free atmosphere CoCl$_2$ (anhydrous, 0.135 g) was dissolved in a minimum of dry THF. 2,6-Diacetylpyridinebis(2-biphenylimine) (0.500 g) was added and the solution darkened and a brown precipitate formed. The mixture was stirred at RT for 2 d after which the volume was reduced and pentane added. The product was filtered off, washed with pentane and dried. Yield 0.500 g.

Experiment 7

[2,6-Pyridinedicarboxaldehydebis (2,6-diisopropylphenylimine)]cobalt[II]dichloride In a dry, oxygen-free atmosphere CoCl$_2$ (anhydrous, 0.072 g) was dissolved in a minimum of dry THF. 2,6-Pyridinedicarboxaldehydebis (2,6-diisopropylphenylimine) (0.256 g) was added and the solution darkened and turned green. The mixture was stirred at RT for 4 d after which the volume was reduced and pentane added. The product was filtered off, washed with benzene and pentane and dried. Yield 0.26 g.

Experiment 8

[2,6-Diacetylpyridinebis(2-t-butylphenylimine)]cobalt[II]dichloride

In a dry, oxygen-free atmosphere CoCl$_2$ (anhydrous, 0.168 g) was dissolved in a minimum of dry THF. 2,6-Diacetylpyridinebis(2-t-butylphenylimine) (0.553 g) was added and the solution darkened and a brown precipitate formed rapidly. The mixture was stirred at RT overnight after which pentane was added. The product was filtered off, washed with pentane and dried. Yield=0.66 g.

In the Examples $^{13}$C NMR spectra were obtained on a Bruker DRX Avance 500 MHz instrument at 30° C. with a Nalorac 10 MM Probe using a 90 degree pulse, digital filtering and digital lock, a spectra width of 29 kHz, an acquisition time of 0.64 sec, and a delay between pulses of 10 sec. Samples were 10 or 20 wt % in CDCl$_3$ with 0.05 M CrAcAc. A variety of 2D NMR experiments were used to support the assignments, including HMQC, HMBC, HSQC-TOCSY, and TOCSY.

In the examples, certain compounds having the formula (II) are used as "Catalysts". In these compounds, $R^1$, $R^2$ and $R^3$ are hydrogen, n is 2, and X is Cl. The remainder of the substituents are given in Table 1.

TABLE 1

| Catalyst No. | $R^4$ | $R^5$ | $R^6$ | $R^7$ |
|---|---|---|---|---|
| 1 | Me | Me | 2-phenylphenyl | 2-phenylphenyl |
| 2 | Me | Me | 2-chloro-6-methylphenyl | 2-chloro-6-methylphenyl |
| 3 | H | H | 2,6-diisopropylphenyl | 2,6-diisopropylphenyl |
| 4 | H | H | 2-phenylphenyl | 2-phenylphenyl |
| 5 | Me | Me | 2-t-butylphenyl | 2-t-butylphenyl |

EXAMPLE 1

Inside a drybox under a nitrogen atmosphere, Catalyst 1 (12.4 mg, 0.02 mmol) was slurried in anhydrous toluene (25 ml) in a Schlenk flask. The flask was sealed, removed from the drybox and placed under an atmosphere of propylene (35 kPa) and cooled to 0° C. The cocatalyst, PMAO (0.5 ml, 9.3wt % Al in toluene, Akzo), was added with vigorous stirring and the reaction allowed to proceed at 0° C. for 5 h after which it was warmed to RT and allowed to react for a further 16 h. The reaction was quenched by addition of MeOH/10% HCl and the toluene phase decanted. Toluene and the lower molecular weight oligomers (up to and including a major portion of the C$_9$ fraction) were removed under vacuum. The remaining oligomers were analyzed using, GC, GC/MS and $^{13}$C-NMR. Yield 2.3 g

| Species | Mol % |
|---|---|
| 1-ene | 8.9 |
| 2-ene trans | 30.1 |
| 2-ene cis | 16.2 |
| 3-ene trans | 1.5 |
| 3-ene cis | ND |
| 4-ene trans | 18.1 |
| 2-methylene | 1.5 |
| 3-methylene | ND |
| 4+-methylene | 1.3 |
| 5+-ene | 22.5 |
| % Me per ene | 3 |
| 1B1/1000CH$_2$ | ~3 |

ND = not detected
% Me per ene: number of methyl branches per double bond occurrence.
1B1/1000 CH$_2$: number of methyl branches per 1000 CH$_2$.

EXAMPLE 2

Inside a drybox under a nitrogen atmosphere, Catalyst 2 (32 mg, 0.06 mmol) was slurried in anhydrous toluene (25 ml) in a Schlenk flask. The flask was sealed, removed from the drybox and placed under an atmosphere of propylene (35 kPa) and cooled to 0° C. The cocatalyst, PMAO (0.5 ml, 9.3 wt % Al in toluene, Akzo), was added with vigorous stirring and the reaction allowed to proceed at 0° C. for 5 h after which it was warmed to RT and allowed to react for a further 16 h. The reaction was quenched by addition of MeOH/10% HCl and the toluene phase decanted. Toluene and the lower molecular weight oligomers (up to and including a major portion of the C$_9$ fraction) were removed under vacuum. The remaining oligomers were analyzed using, GC, GC/MS and $^{13}$C-NMR. Yield=3.7 g The same species present in Example 1 are also present in this sample. The ND species are also the same. However, in this sample there are several additional olefinic resonances. There are about 50–100 1B1 methyls per 1000 methylenes.

EXAMPLE 3

Inside a drybox under a nitrogen atmosphere, Catalyst 3 (35 mg, 0.06 mmol) was slurried in anhydrous toluene (25 ml) in a Schlenk flask. The flask was sealed, removed from the drybox and placed under an atmosphere of propylene (35 kPa) and cooled to 0° C. The cocatalyst, PMAO (0.5 ml, 9.3 wt % Al in toluene, Akzo), was added with vigorous stirring and the reaction allowed to proceed at 0° C. for 5 h after which it was warmed to RT and allowed to react for a further 16 h. The reaction was quenched by addition of MeOH/10% HCl and the toluene phase decanted. GC analysis of this crude reaction product indicated the presence of a small amount of oligomer.

EXAMPLE 4

Inside a drybox under a nitrogen atmosphere, Catalyst 4 (34 mg, 0.06 mmol) was slurried in anhydrous toluene (25 ml) in a Schlenk flask. The flask was sealed, removed from the drybox and placed under an atmosphere of propylene (35 kPa) and cooled to 0° C. The cocatalyst, PMAO (0.5 ml, 9.3 wt % Al in toluene, Akzo), was added with vigorous stirring and the reaction allowed to proceed at 0° C. for 5 h after which it was warmed to RT and allowed to react for a further 16 h. The reaction was quenched by addition of MeOH/10% HCl and the toluene phase decanted. GC analysis of this crude reaction product indicated the presence of a small amount of oligomer.

EXAMPLE 5

Inside a drybox under a nitrogen atmosphere, Catalyst 5 (33 mg, 0.06 mmol) was slurried in anhydrous toluene (25 ml) in a Schlenk flask. The flask was sealed, removed from the drybox and placed under an atmosphere of propylene (35 kPa) and cooled to 0° C. The cocatalyst, PMAO (0.5 ml, 9.3wt % Al in toluene, Akzo), was added with vigorous stirring and the reaction allowed to proceed at 0° C. for 5 h after which it was warmed to RT and allowed to react for a further 16 h. The reaction was quenched by addition of MeOH/10% HCl and the toluene phase decanted. GC analysis of this crude reaction product indicated the presence of a small amount of oligomer.

What is claimed is:

1. A process for the oligomerization of propylene, comprising, contacting, at a temperature of about −100° C. to about +200° C., a compound of the formula

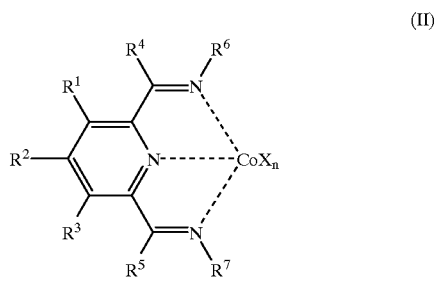

(II)

with propylene and:

(a) a first compound W, which is a neutral Lewis acid capable of abstracting X$^-$ and alkyl group or a hydride group from Co to form WX$^-$, WR$^{20}$ or WH and which is also capable of transferring an alkyl group or a hydride to cobalt, provided that WX$^-$is a weakly coordinating anion; or (b) a combination of a second compound which is capable of transferring an alkyl or hydride group to cobalt and a third compound which is a neutral Lewis acid which is capable of abstracting X$^-$, a hydride or an alkyl group from Co to form a weakly coordinating anion;

wherein:

each X is an anion;

n is 1, 2 or 3 so that the total number of negative charges on said anion or anions is equal to the oxidation state of a Co atom present in (II);

R$^1$, R$^2$ and R$^3$ are each independently hydrogen, hydrocarbyl, substituted hydrocarbyl, or an inert functional group;

R$^4$ and R$^5$ are each independently hydrogen, hydrocarbyl, an inert functional group, or substituted hydrocarbyl;

R$^6$ and R$^7$ are aryl or substituted aryl; and

R$^{20}$ is alkyl.

2. A process for the oligomerization of propylene, comprising contacting, at a temperature of about −100° C. to about +200° C., a Co[II] or Co[III] complex of a tridentate ligand of the formula

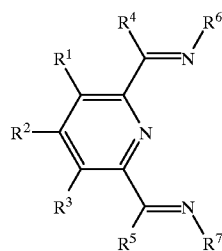

with propylene, wherein:

R$^1$, R$^2$ and R$^3$ are each independently hydrogen, hydrocarbyl, substituted hydrocarbyl, or an inert functional group;

R$^4$ and R$^5$ are each independently hydrogen, hydrocarbyl, an inert functional group or substituted hydrocarbyl; and R$^6$ and R$^7$ are aryl or substituted aryl;

and provided that a Co[II] or Co[III] atom also has bonded to it an empty coordination site or a ligand that may be displaced by said propylene, and a ligand that may add to said propylene.

3. The process as recited in claim 1 or 2 wherein: R$^6$ is

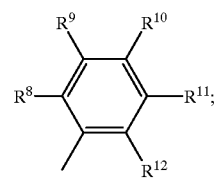

R$^7$ is

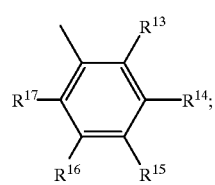

R$^8$ and R$^{13}$ are each independently hydrocarbyl, substituted hydrocarbyl or an inert functional group;

R$^9$, R$^{10}$, R$^{11}$, R$^{14}$, R$^{15}$ and R$^{16}$ are each independently hydrogen, hydrocarbyl, substituted hydrocarbyl or an inert functional group;

R$^{12}$ and R$^{17}$ are each independently hydrogen, hydrocarbyl, substituted hydrocarbyl or an inert functional group;

and provided that any two of R$^8$, R$^9$, R$^{10}$, R$^{11}$, R$^{12}$, R$^{13}$, R$^{14}$, R$^{15}$, R$^{16}$ and R$^{17}$ that are vicinal to one another, taken together may form a ring.

4. The process as recited in claim 3 wherein:

R$^1$, R$^2$ and R$^3$ are hydrogen;

R$^9$, R$^{10}$ R$^{11}$, R$^{14}$, R$^{15}$ and R$^{16}$ are each independently halogen, alkyl containing 1 to 6 carbon atoms, or hydrogen;

R$^8$ and R$^{13}$ is each independently halogen, phenyl or alkyl containing 1 to 6 carbon atoms;

R$^{12}$ and R$^{17}$ are each independently halogen, phenyl, hydrogen, or alkyl containing 1 to 6 carbon atoms; and R$^4$ and R$^5$ are each independently hydrogen or alkyl containing 1 to 6 carbon atoms.

5. The process as recited in claim 4 wherein R$^9$, R$^{10}$, R$^{11}$, R$^{14}$, R$^{15}$, and R$^{16}$ are each hydrogen.

6. The process as recited in claim 4 wherein R$^8$ and R$^{13}$ are each alkyl containing 1–6 carbon atoms or phenyl, and R$^{12}$ and R$^{17}$ are hydrogen.

7. The process as recited in claim 6 wherein R$^4$ and R$^5$ are each hydrogen or methyl.

8. The process as recited in claim 4 wherein X is chloride, bromide or tetrafluoroborate.

9. The process as recited in claim 4 wherein said neutral Lewis acid is an alkyl aluminum compound.

10. The process as recited in claim 9 wherein said alkyl aluminum compound is polymethylaluminoxane.

11. The process as recited in claim 4 wherein said temperature is about −50° C. to about 100° C.

12. The process as recited in claim 1 or 2 wherein a pressure of said propylene is about atmospheric pressure to about 275 MPa.

13. The process as recited in claim 1 wherein R$^{20}$ contains 1 to 4 carbon atoms.

14. The process as recited in claim 4 wherein R$^1$, R$^2$, R$^3$, R$^9$, R$^{10}$, R$^{11}$, R$^{14}$, R$^{15}$ and R$^{16}$ are hydrogen, R$^8$ and R$^{13}$ are chloro, and R$^4$, R$^5$, R$^{12}$ and R$^{17}$ are methyl.

15. The process as recited in claim 4 wherein R$^1$, R$^2$, R$^3$, R$^9$, R$^{10}$, R$^{11}$, R$^{12}$, R$^{14}$, R$^{15}$, R$^{16}$, and R$^{17}$ are hydrogen, R$^4$ and R$^5$ are methyl, and R$^8$ and R$^{13}$ are phenyl.

16. The process as recited in claim 4 wherein R$^1$, R$^2$, R$^3$, R$^4$, R$^5$, R$^9$, R$^{10}$, R$^{11}$, R$^{12}$, R$^{14}$, R$^{15}$, R$^{16}$ and R$^{17}$ are hydrogen, and R$^8$ and R$^{13}$ are phenyl.

17. The process as recited in claim 4 wherein R$^1$, R$^2$, R$^3$, R$^4$, R$^5$, R$^9$, R$^{10}$, R$^{11}$, R$^{14}$, R$^{15}$, and R$^{16}$ are hydrogen, and R$^8$, R$^{12}$, R$^{13}$ and R$^{17}$ are i-propyl.

18. The process as recited in claim 4 wherein R$^1$, R$^2$, R$^3$, R$^9$, R$^{10}$, R$^{11}$, R$^{12}$, R$^{14}$, R$^{15}$, R$^{16}$ and R$^{17}$ are hydrogen, R$^4$ and R$^5$ are methyl, and R$^8$ and R$^{13}$ are t-butyl.

* * * * *